(12) United States Patent
Suga et al.

(10) Patent No.: US 6,502,250 B2
(45) Date of Patent: Jan. 7, 2003

(54) SANITARY PANTY

(75) Inventors: Ayami Suga, Kagawa (JP); Mitsuhiro Wada, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 52 days.

(21) Appl. No.: 09/812,801

(22) Filed: Mar. 20, 2001

(65) Prior Publication Data

US 2001/0025387 A1 Oct. 4, 2001

(30) Foreign Application Priority Data

Mar. 31, 2000 (JP) ........................................ 2000-096854

(51) Int. Cl.$^7$ ............................................... A41B 9/00
(52) U.S. Cl. ...................................... 2/406; 624/385.02
(58) Field of Search ............................ 2/400, 402, 403, 2/406, 401, 228, 238; 604/385.1–402

(56) References Cited

U.S. PATENT DOCUMENTS

| | | | | |
|---|---|---|---|---|
| 2,616,427 A | * | 11/1952 | Pettit | 604/385.1 |
| 3,687,141 A | * | 8/1972 | Matsuba | 604/385.1 |
| RE28,483 E | * | 7/1975 | Ralph | 604/385.1 |
| 4,355,425 A | * | 10/1982 | Jones et al. | 2/402 |
| 4,892,536 A | * | 1/1990 | Des Marais et al. | 604/385.2 |
| 5,855,573 A | * | 1/1999 | Johanson | 604/385.2 |
| 5,940,887 A | * | 8/1999 | Rajala et al. | 2/400 |

FOREIGN PATENT DOCUMENTS

JP        4-92222        8/1992

\* cited by examiner

Primary Examiner—Gloria M. Hale
(74) Attorney, Agent, or Firm—Darby & Darby

(57) ABSTRACT

Provided is a sanitary panty including a front part, a back part, a crotch part located between the front part and the back part, a waist portion formed by an upper edge portion of the front part and an upper edge portion of the back part, a pair of leg openings defined below joining portions of both side edges of the front part and both side edges of the back part, a suspending member extending over the front part, the crotch part and the back part in a longitudinal direction, and an extension cloth extending from both sides of the suspending member located at least in the crotch part and the back part. The suspending member is gradually reduced a width from the waist portion to the crotch part in the back part. The suspending member has greater elastic modulus in a longitudinal direction than that in a lateral direction.

8 Claims, 5 Drawing Sheets

SANITARY PANTY

An entire disclosure and claims in the commonly owned U.S. patent application Ser. No. 09/799,421 entitled "SANITARY PANTY", filed on Mar. 5, 2001, is herein incorporated by reference.

BACKGROUND OF THE INVENTION

1. Field of the Invention

The present invention relates to a sanitary panty with superior wear ability and wearing comfort.

2. Description of the Related Art

A sanitary panty typically has a structure, in which a water-proof sheet is sewn on inner side of crotch cloth portion of a general panty for preventing leakage and external extruding of menstrual blood. Since the sanitary panty is required to prevent side leakage or so forth due to motion of body or variation of attitude in sporting and sleeping, various measures have been taken in sewing position and dimension of the water-proof sheet. Various measures have also been taken for overall structure of the sanitary panty for providing superior wear ability and wearing comfort of a sanitary napkin.

Japanese Registered Utility Model No. 2554676 discloses a sanitary panty taken a measure set forth above. FIGS. 5A and 5B are a front elevation and a back elevation of a sanitary panty of the type disclosed in the above-identified publication.

The sanitary panty illustrated in FIGS. 5A and 5B is formed with a cloth 1a forming a front part and a crotch part, cloth 1b forming a center portion of a back part, and cloths 2 forming both side portions of the front part and the back part. The cloths 1a, 1b and 2 have smaller tensile strength in a longitudinal direction than that in a lateral direction. On the other hand, the tensile strength in the longitudinal direction of the cloths 1a and 1b is greater than that of the cloths 2.

The conventional sanitary panty is designed so that the overall panty may be tightly fitted on a wearer's body by differentiating tensile strength between the cloths 1a and 1b located at laterally center portion and the cloths 2 located at laterally side portions. While the shown panty is designed to be tightly fitted on the wearer's body as a whole, a measure has not been taken for penetrating the crotch part along the wearer's body. Namely, in the crotch part, a lateral stretching force acts on the panty to make it impossible to apply a force urging the center portion of a sanitary napkin toward the wearer's body. Therefore, the conventional sanitary panty cannot achieve a function for tightly fitting the panty onto the wearer's body with deforming the sanitary napkin in convex form (i.e., generally reverse V-shaped cross-section) adapting to the shape of the body.

SUMMARY OF THE INVENTION

Therefore, it is an object of the present invention to provide a sanitary panty which can be well fitted on a wearer's body without causing disposition of a sanitary napkin.

Another object of the present invention is to provide a sanitary panty which can permit tight fititing of the sanitary napkin onto a wearer's body in convex shape.

According to the first aspect of the present invention, a sanitary panty comprises:

a front part;
a back part;
a crotch part located between the front part and the back part;
a waist portion formed by an upper edge portion of the front part and an upper edge portion of the back part;
a pair of leg openings defined below joining portions of both side edges of the front part and both side edges of the back part;
a suspending member extending over the front part, the crotch part and the back part in a longitudinal direction;
an extension cloth extending from both sides of the suspending member located at least in the crotch part and the back part,
the suspending member being gradually reduced a width from the waist portion to the crotch part in the back part, and
the suspending member having greater elastic modulus in a longitudinal direction than that in a lateral direction.

The sanitary panty may further comprise an elastic member mounted on the waist portion, and the suspending member has an elastic modulus in the longitudinal direction at least in the vicinity of a center line smaller than that in a circumferential direction of the elastic member. The extension cloth may be formed with a non-stretchable material or a stretchable material having smaller elastic modulus in the longitudinal and lateral directions in comparison with the suspending member. The extension cloth may be provided on both sides of the suspending member over the front part, the crotch part and the back part, and the leg openings are formed with the material of the extension cloth.

According to the second aspect of the present invention, a sanitary panty comprises:

a front part;
a back part;
a crotch part located between the front part and the back part;
a waist portion formed by an upper edge portion of the front part and an upper edge portion of the back part;
a pair of leg openings defined below joining portions of both side edges of the front part and both side edges of the back part;
a suspending member extending over the front part, the crotch part and the back part in a longitudinal direction;
an extension cloth extending from both sides of the suspending member located at least in the crotch part and the back part,
the suspending member being gradually reduced a width from the waist portion to the crotch part in the back part, and
the suspending member having greater contraction stress in a longitudinal direction than that in a lateral direction, in the worn condition or in a three-dimensional shape approximated with the worn condition.

The sanitary panty may further comprise an elastic member mounted on the waist portion, and the suspending member has a contraction stress in the longitudinal direction at least in the vicinity of a center line smaller than that in a circumferential direction of the elastic member. The extension cloth may be formed with a non-stretchable material, or a stretchable material having smaller contraction stress in the longitudinal and lateral directions in comparison with the suspending member. The extension cloth may be provided on both sides of the suspending member over the front part, the crotch part and the back part, and the leg openings are formed with the material of the extension cloth.

As set forth above, the suspending member is provided the greater elastic modulus in the longitudinal direction than that in the lateral direction. On the other aspect of the invention, the suspending member is provided greater contraction stress in the longitudinal direction than that in the lateral direction. In either case, according to the present invention, the center portion of the crotch part is pulled up to deform the sanitary napkin in upwardly projecting convex shape to permit firm fitting with the wearer's body to successfully prevent side leakage of menstrual blood. Also, since the elastic modulus and the contraction stress of the elastic member on the waist portion are greater than those of the suspending member in the longitudinal direction, the sanitary panty will never cause slacking down as worn.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Incorporation by Reference

An entire disclosure and claims in the commonly owned co-pending U.S. Patent Application Serial No. (not yet known), entitled "SANITARY PANTY", filed with claiming convention priority based on Japanese Patent Application No. 2000-60267, filed on Mar. 6, 2000, is herein incorporated by reference.

Figure 1A:
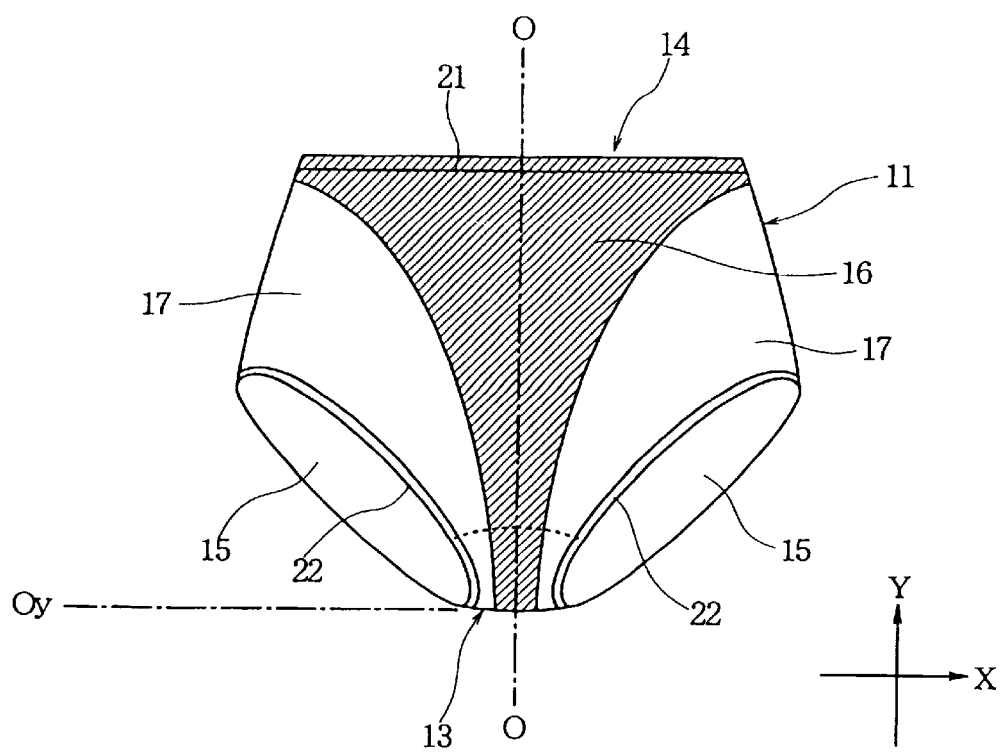
FIGS. 1A and 1B are front elevation and back elevation of the first embodiment of a sanitary panty according to the present invention.
Figure 1B:
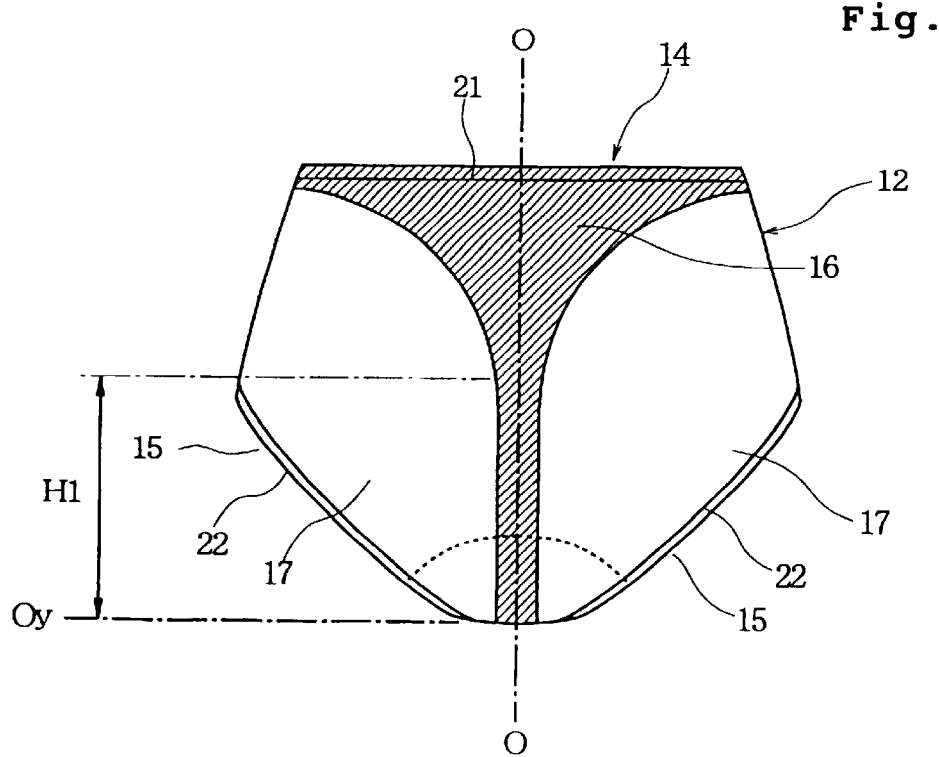
Figure 2:
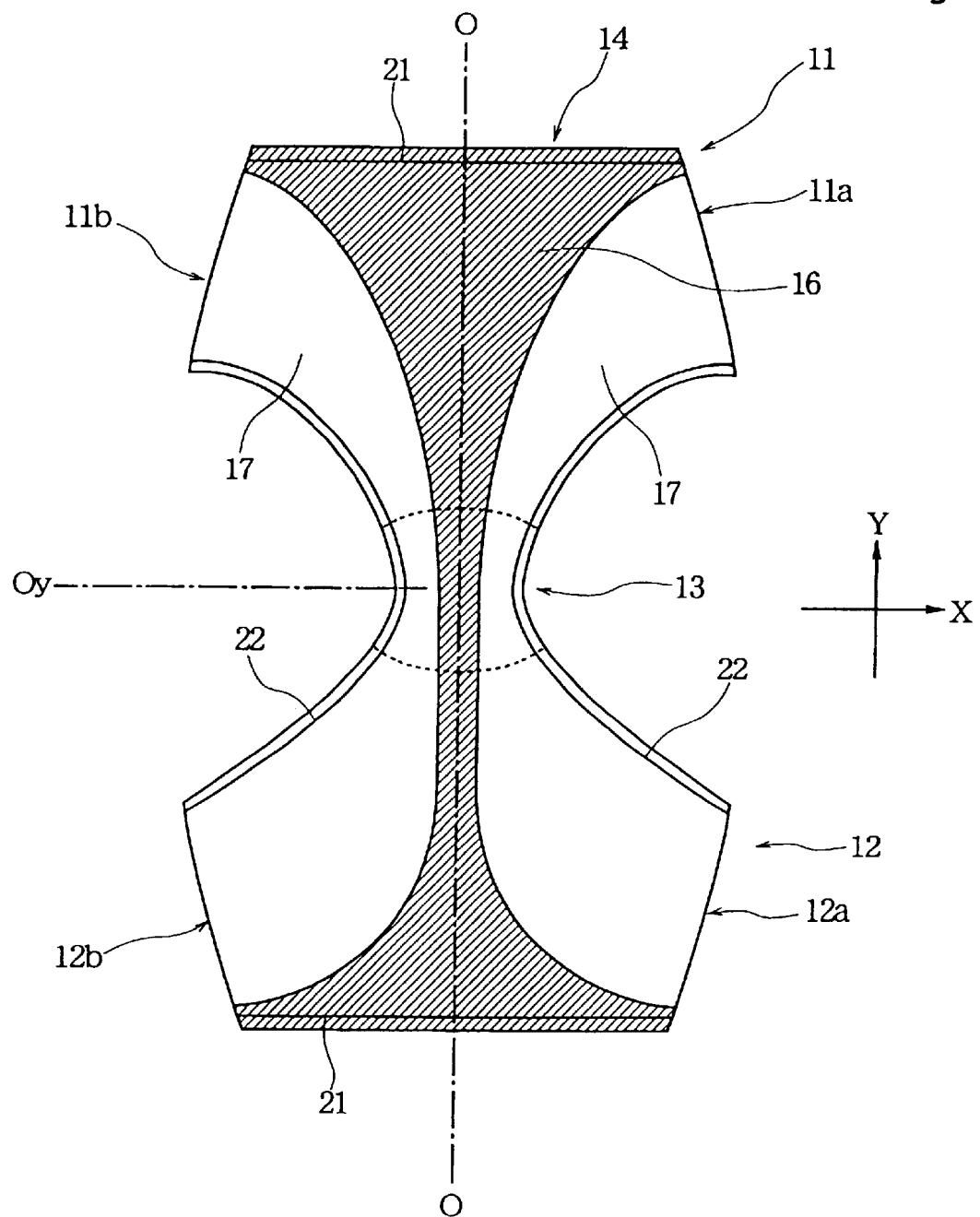
FIG. 2 is a development elevation of the sanitary panty of FIGS. 1A and 1B.

FIGS. 1A, 1B and 2 show the first embodiment of a sanitary panty according to the present invention, in which FIG. 1A is a front elevation and FIG. 1B is a back elevation, and FIG. 2 is a development elevation thereof.

The sanitary panty shown in FIGS. 1A, 1B and 2 is generally formed with a front part 11, a back part 12 and a crotch part 13.

In FIGS. 1A, 1B and 2, Y direction along which the front part 11, the crotch part 13 and the back part 12 are formed in series is referred to as a longitudinal direction, and X direction transverse to the Y direction is referred to as a lateral direction. A centerline extending in the longitudinal direction at a center in the lateral direction is taken as O-O.

As shown in FIG. 2, a side edge 11a of the front part 11 and a side edge 12a of the back part 12 are sewn and a side edge 11b of the front part 11 and a side edge 12b of the back part 12 are sewn to form a sanitary panty having a waist portion 14 and leg openings 15.

In a laterally center region of the panty, a stretchable suspending member 16 extending in the longitudinal direction along a center line O-O. In the back part 12, the suspending member 16 is shaped to gradually reduce the width from the waist portion 14 to the crotch part 13. Similarly, in the front part 11, the suspending member 16 is shaped to gradually reduce the width from the waist portion 14 to the crotch part 13.

On both sides of the suspending member 16, extension cloths 17 are provided. The suspending member 16 and the extension cloths 17 are formed with different cloths. The extension cloths 17 and the suspending member 16 may be sewn at the boundaries thereof. In the alternative, the entire panty may be formed with the cloth of the extension cloth 17 and the suspending member 16 may be sewn at the center portion thereof overlapping with the corresponding portion formed with the cloth forming the entire panty.

In the first embodiment shown in FIGS. 1A, 1B and 2, the extension cloths 17 are extended laterally on both sides of the suspending member 16 in the front part 11, the back part 12 and the crotch part 13. In a form of panty, the extension cloths 17 define leg openings 15. On the other hand, in the waist portion 14, the suspending member 16 of the front part 11 and the suspending member 16 of the back part 12 are jointed to form the entire waist portion with the stretchable material of the suspending member 16. However, it is not essential to form the entire waist portion with the stretchable material of the suspending member 16. In the alternative, it is possible to extend the extension cloth 17 even in the waist portion so that the extension cloths 17 in the waist portion 14 are joined to form the waist portion.

In the waist portion 14, one or more strip or string form elastic members 21 are mounted along the waist portion to form an elastic waist holding portion. Even on the leg openings 15, one or more strip or string form elastic members 22 are mounted along the leg openings 15 to form elastic leg holding portions.

The entire suspending member 16 is formed with a woven fabric fabricated with stretchable yarn or fiber, or a woven fabric sewn elastic stretchable material such as rubber in the longitudinal direction (Y direction) and the lateral direction (X direction). The suspending member 16 has greater elastic modulus in the longitudinal direction than that in the lateral direction. Namely, contraction stress at the time when the stretchable material forming the suspending member 16 is cut into a predetermined lateral width and is applied a predetermined distortion in the longitudinal direction, is greater than the contraction stress at the time when the stretchable material forming the suspending member 16 is cut into the same longitudinal width (i.e., the length) and is applied a predetermined distortion in the lateral direction thereof.

Accordingly, when the sanitary panty is worn on the wearer's body or is formed into a three-dimensional shape approximated with the worn condition (when comparable expansion as that applied in worn condition is applied to the panty in both longitudinal and lateral directions), the contraction stress (the tension force per a predetermined width) in longitudinal direction of the suspending member 16 becomes greater than the contraction stress in the lateral direction thereof.

The suspending member 16 is continuous in the front part 11, the back part 12 and the crotch part 13 in the longitudinal direction. Also, the suspending member 16 is shaped to have a narrow width in the lowermost end portion Oy of the crotch part 13. Accordingly, when the sanitary panty is worn on the wearer's body, in the suspending member 16 mating with the crotch part 13, the contraction stress in the longitudinal direction becomes greater than that in the lateral direction, for example, in the extent greater than or equal to about 1.5 times and smaller than or equal to about 8 times. Accordingly, when the sanitary napkin is fitted on inside of the sanitary panty in the crotch part 13, a large urging force is applied at the center line O-O of the sanitary napkin.

On the other hand, as shown in FIG. 1B, in the three-dimensional shape of the sanitary panty, the suspending member 16 in the back part 12 is provided the same or substantially the same width as that in the crotch part 13 from the lowermost end Oy to a height H1. This portion having a narrow width may penetrate into a gluteal cleft so that the suspending member 16 may be tightly fitted onto the crotch part 13. Accordingly, the sanitary napkin fitted in the crotch part is tightly fitted on the wearer's body. Furthermore, since a tension force is applied along the center line O-O of the sanitary panty, the lateral center portion of the sanitary napkin is deformed into convex shape penetrating into the crotch part of the wearer. Accordingly, the sanitary napkin can be firmly fitted on the crotch part of the wearer's body. Therefore, side leakage of the menstrual blood is hardly caused and disposition of the sanitary napkin is hardly caused.

On the other hand, when the sanitary panty is worn on the wearer's body, even if the suspending member 16 is stretched laterally, due to difference of the elastic modulus, large contraction stress can be caused in the longitudinal direction to permit creation of tension force along the center line O-O as set forth above. Namely, even if the expansion is applied in the lateral direction upon wearing of the sanitary panty, the suspending member 16 may be stretched relatively freely in the lateral direction and may constantly apply large contracting force in the longitudinal direction. Therefore, the sanitary napkin fitted on the crotch part is upwardly urged by large tension force along the center line O-O for firmly fitting on the wearer's body.

On the other hand, the elastic member 21 forming the waist holding portion is mounted on the waist portion 14. The elastic modulus in the longitudinal direction at least in the vicinity of the center line O-O is preferably smaller than the elastic modulus in the waist direction of the elastic member 21 ("the waist direction" is also referred to as a circumferential direction). On the other hand, in the worn condition or in the three-dimensional shape approximated with the worn condition as shown in FIGS. 1A and 1B, contraction stress of the suspending member 16 in the longitudinal direction around the center line O-O is preferably smaller than the contraction stress of the elastic member 21.

With such construction, the waist portion 14 may not be pulled downwardly in significant magnitude by the contracting force of the suspending member 16 to hardly cause slacking of the sanitary panty upon wearing of the sanitary panty. It should be noted that the elastic modulus becomes a total value of the elastic modulus of one or more elastic members 16, when the elastic member 21 is one or more. On the other hand, the contraction stress represents a difference between a contracting tension force created when a predetermined distortion is applied to all of one or more elastic members 21 having a predetermined width and a contracting tension force created when the same distortion is applied to the suspending member 16 in the same width as the one or more elastic members 21, in the longitudinal direction.

Next, it is preferred that the extension cloth 17 may not apply large lateral tension force to the suspending member 16 at the crotch part 13. When large lateral tension force is applied to the suspending member 16 in the crotch part 13, the longitudinal tension force applied along the center line O-O urging the center portion of the sanitary napkin toward the wearer's body can be reduced to cause difficulty in deforming the sanitary napkin in convex shape and in tight fitting of the sanitary napkin onto the wearer's body.

Furthermore, the extension cloth 17 is preferably not created large contracting force in the longitudinal direction in comparison with the suspending member 16. If large contracting force is created in the longitudinal direction in the extension cloth 17 during wearing, both side portions of the waist portion 14, namely portion contacting with hip born, is pulled downwardly to easily cause slacking of the sanitary panty.

As set forth above, it is preferred that the extension cloth 17 is formed with a non-stretchable material or a material having smaller elongation amount (maximum distortion) than that of the suspending member 16. Namely, expansion upon wearing is mainly provided by the suspending member 16, and the extension cloth 17 has little expansion. Difference of stresses in the longitudinal direction and the lateral direction is preferably caused only by the suspending member 16. In the alternative, when the extension cloth 17 is formed with a stretchable material, the stretchable material should be stretched quite easily and thus have smaller elastic modulus in longitudinal direction and lateral direction in comparison with the suspending member 16. In this case, upon wearing to the body, the extending cloth 17 may also cause expansion. The stress caused by expansion is smaller so as not to prevent large contraction stress of the suspending member 16 in the longitudinal direction.

Figure 3A:
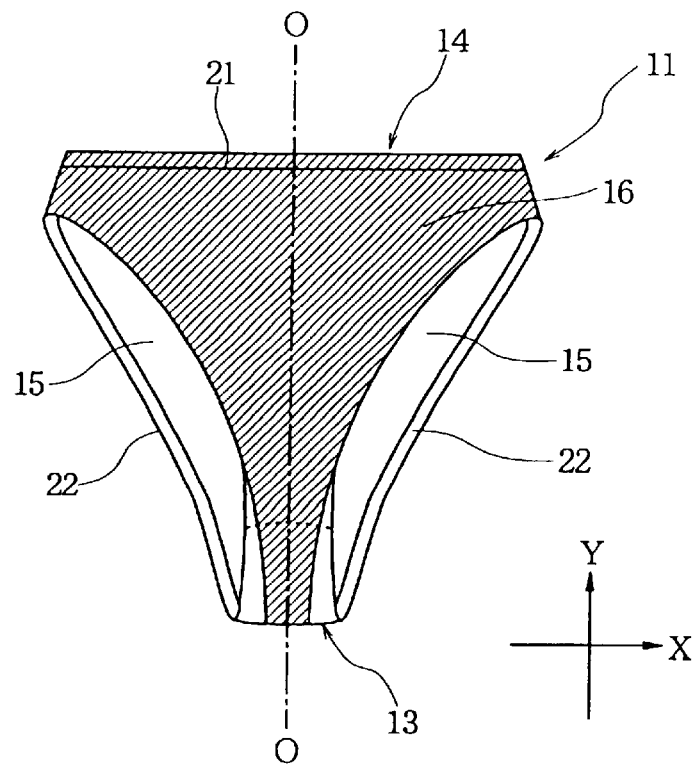
FIGS. 3A and 3B are front elevation and back elevation of the second embodiment of a sanitary panty according to the present invention.
Figure 3B:
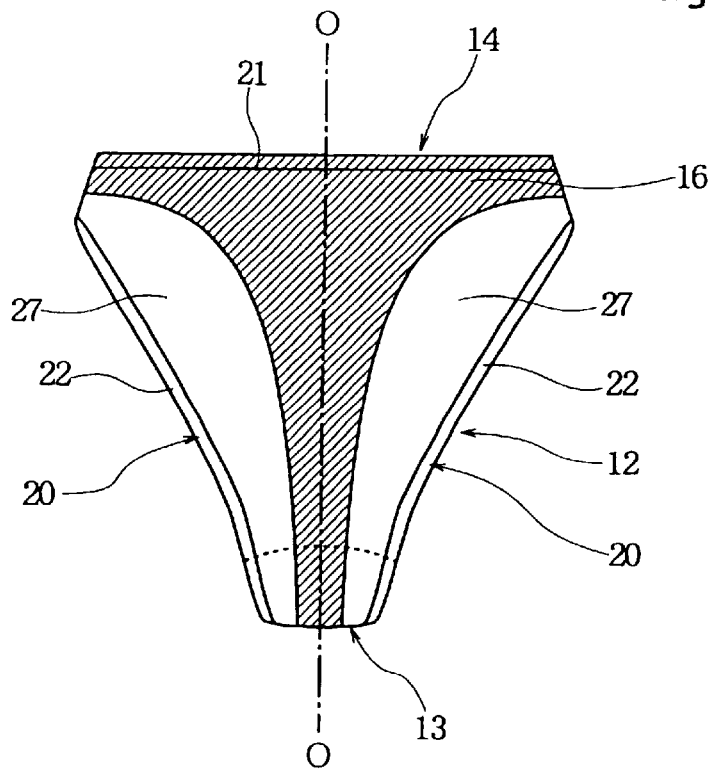
Figure 4:
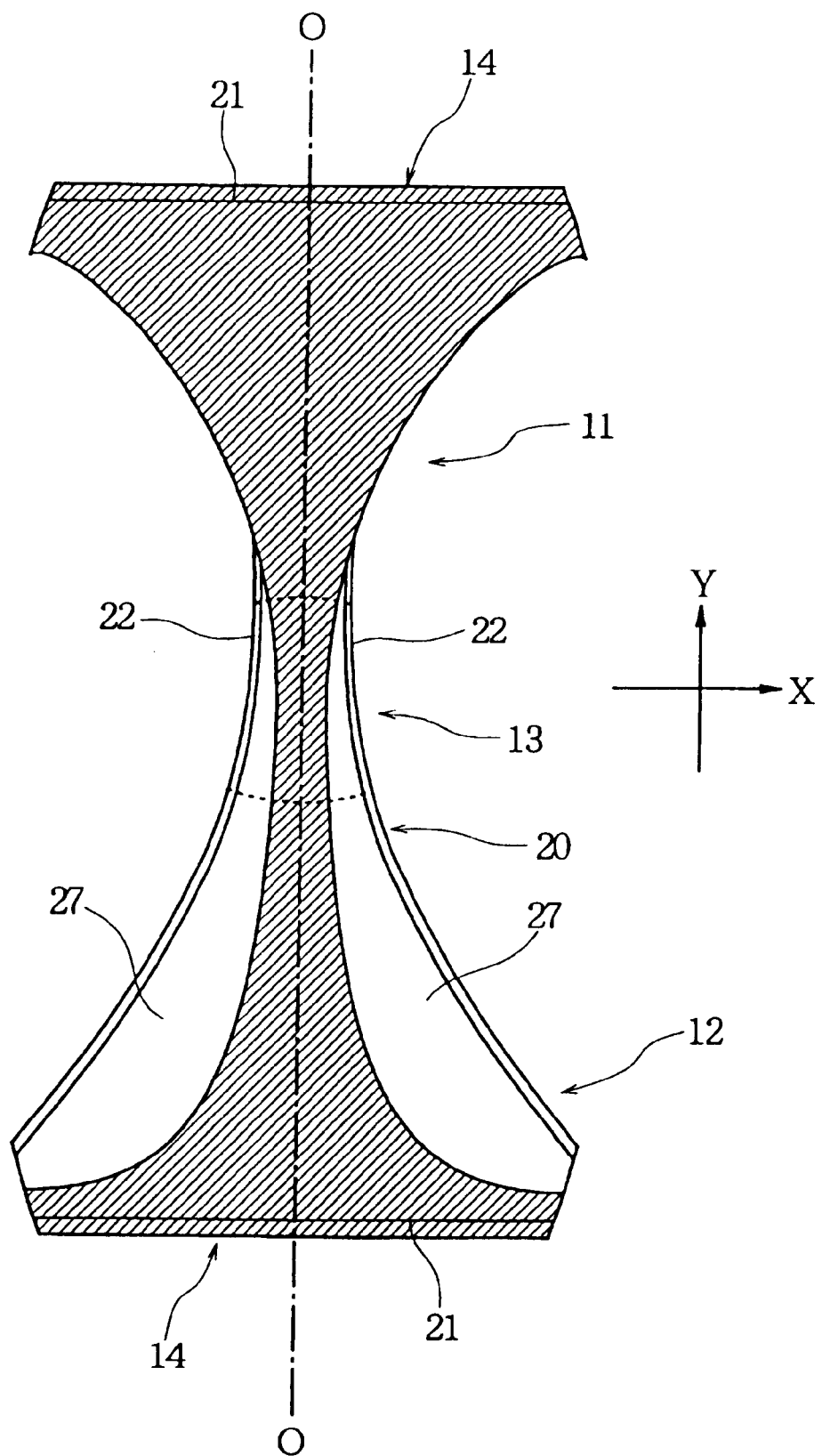
FIG. 4 is a development elevation of the sanitary panty of FIGS. 3A and 3B.
Figure 5A:
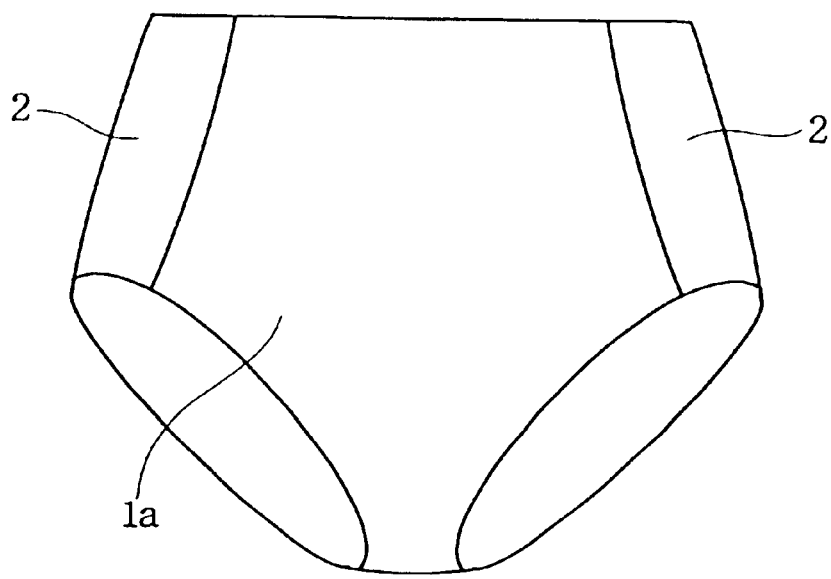
FIGS. 5A and 5B are front elevation and back elevation of the conventional sanitary panty.
Figure 5B:
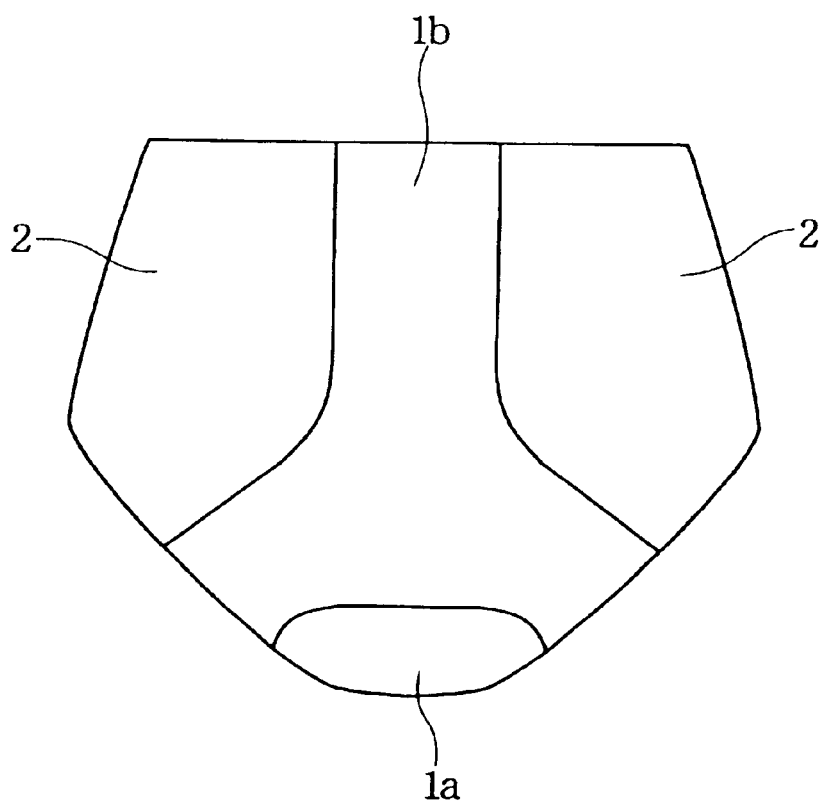

FIGS. 3A, 3B and 4 show the second embodiment of the sanitary panty according to the present invention, in which FIG. 3A is a front elevation of the second embodiment of the sanitary panty according to the present invention, FIG. 3B is a back elevation thereof and FIG. 4 is development elevation thereof.

In the sanitary panty shown in FIGS. 3A, 3B and 4, the suspending member 16 of substantially the same shape shown in FIGS. 1A, 1B and 2 are provided. Elastic modulus and contraction stress in the longitudinal direction and the lateral direction of the suspending member 16 are the same as the first embodiment.

In the embodiment shown in FIGS. 3A, 3B and 4, extension cloths 27 formed with the same material as the extension cloth 17 of FIGS. 1A and 1B are provided. The extension cloths 27 are extended from both side portions of the suspending member 16. In the embodiment shown in FIGS. 3A, 3B and 4, the extension cloths 27 are provided only on both sides from the portion close to the boundary between the front part 11 and the crotch part 13 to the suspending member 16 of the back part 12. No extension cloth 27 is provided in the front part 11.

In the sanitary panty formed as illustrated in FIGS. 3A and 3B, both lateral edge portions of the suspending member 16 in the front part 11 and both lateral edge portions of the suspending member 16 in the back part 12 are joined to form the waist portion 14. Thus, the entire length of the waist portion 14 is formed with the material of the suspending member 16.

Similarly to the former embodiment, the elastic members 21 and 22 are provided on the waist portion 14 and the leg openings 15.

The suspending member 16, the waist member 14 and the extension cloths 27 in the second embodiment of the sanitary panty shown in FIGS. 3A, 3B and 4 are formed with stretchable materials having the same or similar property as those of the first embodiment of the sanitary panty of FIGS. 1A, 1B and 2. Therefore, the sanitary napkin fitted to the crotch part 13 can be firmly fitted on the wearer's body.

As set forth above, by forming the sanitary panty formed with the materials set forth above, the center portion of the sanitary napkin can be deformed in convex shape to be firmly fitted on the wearer's body.

The sanitary napkin thus firmly fitted will hardly cause disposition in lateral direction, hardly cause side leakage of menstrual blood from the sanitary napkin, and hardly cause side leakage of menstrual blood from the sanitary panty.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary panty comprising: a front part;
    a back part;
    a crotch part located between said front part and said back part;
    a waist portion formed by an upper edge portion of said front part and an upper edge portion of said back part;
    a pair of leg openings defined below joining portions of both side edges of said front part and both side edges of said back part;
    a suspending member extending over said front part, said crotch part and said back part in a longitudinal direction; an extension cloth extending from both sides of said suspending member located at least in said crotch part and said back part,
    said suspending member being gradually reduced in width from said waist portion to said crotch part in said back part, and
    said suspending member having greater elastic modulus in said longitudinal direction than that in a lateral direction perpendicular to said longitudinal direction.

2. A sanitary panty as set forth in claim 1, which further comprises an elastic member mounted on said waist portion and extending in a circumferential direction along said waist portion, and said elastic modulus of said suspending member in said longitudinal direction is smaller than an elastic modulus of said elastic member in said circumferential direction.

3. A sanitary panty as set forth in claim 1, wherein said extension cloth is formed with a non-stretchable material, or a stretchable material having smaller elastic modulus in the longitudinal and lateral directions in comparison with said suspending member.

4. A sanitary panty as set forth in claim 1, wherein said extension cloth is provided on both sides of said suspending member over said front part, said crotch part and said back part, and said leg openings are formed with the material of said extension cloth.

5. A sanitary panty comprising: a front part;
    a back part;
    a crotch part located between said front part and said back part;
    a waist portion formed by an upper edge portion of said front part and an upper edge portion of said back part;
    a pair of leg openings defined below joining portions of both side edges of said front part and both side edges of said back part;
    a suspending member extending over said front part, said crotch part and said back part in a longitudinal direction;
    an extension cloth extending from both sides of said suspending member located at least in said crotch part and said back part,
    said suspending member being gradually reduced in width from said waist portion to said crotch part in said back part, and
    said suspending member having a greater force of contraction in said longitudinal direction than that in a lateral direction perpendicular to said longitudinal direction, in the worn condition or in a three-dimensional shape approximated with the worn condition.

6. A sanitary panty as set forth in claim 5, which further comprises an elastic member mounted on said waist portion and extending in a circumferential direction along said waste portion, and said force of contraction of said suspending member in said longitudinal direction is smaller than the force of contraction of said elastic in said circumferential direction.

7. A sanitary panty as set forth in claim 5, wherein said extension cloth is formed with a non-stretchable material, or a stretchable material having smaller contraction stress in the longitudinal and lateral directions in comparison with said suspending member.

8. A sanitary panty as set forth in claim 5, wherein said extension cloth is provided on both sides of said suspending member over said front part, said crotch part and said back part, and said leg openings are formed with the material of said extension cloth.

* * * * *

UNITED STATES PATENT AND TRADEMARK OFFICE
CERTIFICATE OF CORRECTION

PATENT NO.     : 6,502,250 B2
DATED          : January 7, 2003
INVENTOR(S)    : Ayami Suga et al.

It is certified that error appears in the above-identified patent and that said Letters Patent is hereby corrected as shown below:

<u>Column 8,</u>
Line 43, delete "waste" and substitute -- waist --;
Line 45, delete "the" and substitute -- a --;
Line 46, after "elastic" insert -- member --.

Signed and Sealed this

Third Day of June, 2003

JAMES E. ROGAN
*Director of the United States Patent and Trademark Office*